United States Patent [19]

Miller et al.

[11] 4,421,922

[45] Dec. 20, 1983

[54] PROCESS FOR THE PRODUCTION OF TETRONIC ACID

[75] Inventors: Raimund Miller, Hackensack, N.J.; Leander Tenud, Visp, Switzerland

[73] Assignee: Lonza Ltd., Gampel, Switzerland

[21] Appl. No.: 388,431

[22] Filed: Jun. 14, 1982

[30] Foreign Application Priority Data

Jun. 17, 1981 [CH] Switzerland .................. 3983/81

[51] Int. Cl.$^3$ ............................................ C07D 307/60
[52] U.S. Cl. ................................................ 549/313
[58] Field of Search ........................................ 549/313

[56] References Cited

U.S. PATENT DOCUMENTS

| Re. 28,242 | 11/1974 | Boosen | 549/313 |
| 3,210,377 | 10/1965 | Machleidt | 549/313 |
| 3,824,255 | 7/1974 | Boosen | 549/313 |

FOREIGN PATENT DOCUMENTS

| 2143709 | 3/1972 | Fed. Rep. of Germany . |
| 503722 | 2/1971 | Switzerland . |
| 529128 | 10/1972 | Switzerland . |

OTHER PUBLICATIONS

"The Total Synthesis of the Antibiotic Malonomicin", Tetrahedron, vol. 34, (1978), pp. 223 to 231, by Baan et al.

*Primary Examiner*—Norma S. Milestone
*Attorney, Agent, or Firm*—Fisher, Christen & Sabol

[57] ABSTRACT

Process for the production of tetronic acid from 4-haloacetoacetic ester which begins by converting a 4-haloacetoacetic ester into the corresponding 4-benzyloxyacetoacetic ester. The 4-benzyl ester is then hydrogenolyzed into an intermediate product. The 4-hydroxyacetoacetic ester is converted by treatment with acid into tetronic acid. The 4-hydroxyacetoacetic ester can be isolated before conversion. The 4-benzyloxyacetoacetic ester can be produced by conversion of the 4-haloacetoacetic ester with a metal salt of benzyl alcohol. The hydrogenolysis can be carried out in the presence of an acid, whereby the 4-hydroxyacetoacetic ester forming in situ is rearranged directly into tetronic acid. The hydrogenolysis can be carried out under pressure in the presence of a hydrogenation catalyst.

22 Claims, No Drawings

PROCESS FOR THE PRODUCTION OF TETRONIC ACID

BACKGROUND OF THE INVENTION

1. Field of The Invention

The invention relates to a process for the production of tetronic acid from 4-haloacetoacetic ester.

2. Prior Art

Tetronic acid, which is used among other things as an accelerator for photographic development, is known to be produced from 4-mono-haloacetoacetic ester or acid. According to the Swiss Pat. No. 503,722, 4-chloroacetoacetic ester is reacted with an aromatic amine to produce 3-arylaminocrotolactone, and the tetronic acid is liberated from such lactone by means of a mineral acid. The disadvantage of such method is that the isolation of the tetronic acid can only be realized by means of high vacuum sublimation. According to Swiss Pat. No. 529,128, 4-haloacetoacetic acid is reacted with an alkali in an aqueous solution. By treatment with a mineral acid the tetronic acid is liberated. Here too the isolation of the tetronic acid must be accomplished by means of high vacuum sublimation; moreover, the achieved yield is only 43 to 44 percent.

BROAD DESCRIPTION OF THE INVENTION

An object of the invention is to provide a process for the production of tetronic acid from 4-haloacetoacetic ester. Another object is to provide such a process which avoids the above-stated disadvantages of the prior art. A further object of the invention is to provide certain new compositions. Other objects and advantages of this invention are set out herein or are obvious to one ordinarily skilled in the art.

The objects and advantages of this invention are achieved by the process and compound of this invention.

This invention involves a process for the production of tetronic acid from 4-haloacetoacetic ester. The 4-haloacetoacetic ester is converted into the corresponding 4-benzyloxyacetoacetic ester. Such 4-benzyloxy ester is hydrogenolyzed into the corresponding 4-hyroxyacetoacetic ester, as an intermediate product. Then the 4-hydroxyacetoacetic ester is converted into tetronic acid by treatment with an acid. The 4-hydroxyacetoacetic ester can be isolated, with the acid treatment being carried out after such isolation. Preferably the 4-benzyloxyacetoacetic ester is produced by conversion of 4-haloacetoacetic ester using a metal salt of the benzyl alcohol. Advantageously the hydrogenolysis is carried out under pressure in the presence of a hydrogenation catalyst. Preferably the hydrogenolysis is carried out in the presence of an acid, whereby the 4-hydroxyacetoacetic ester forming in situ is rearranged directly into the tetronic acid.

The invention also includes a composition composed of a metal salt of benzyl alcohol, a 4-haloacetoacetic ester and an organic salt.

DETAILED DESCRIPTION OF THIS INVENTION

As used herein, all parts, ratios, percentages and proportions are on a weight basis, unless otherwise stated herein or otherwise obvious herefrom to one ordinarily skilled in the art.

Examples of the 4-haloacetoacetic esters are the 4-bromo- and 4-chloro-derivatives, with the 4-chloro-derivatives being preferred. Examples of such esters are those formed from alcohols having 1 to 6 carbon atoms, such as, methyl alcohol, ethyl alcohol, propyl alcohol and butyl alcohol. Preferably 4-chloroacetoacetic ethyl ester is used as the starting material.

The conversion of the 4-haloacetoacetic ester into the 4-benzyloxyacetoacetic ester is done effectively by allowing an alkali salt, preferably the sodium salt, of benzyl alcohol to act on the 4-haloacetoacetic ester in an organic solvent. Examples of useful alkali salts of benzyl alcohol are the potassium salt and the lithium salt. Any suitable organic compound can be used as the solvent; advantageously, however, dimethyl sulfoxide or tetrahydrofuran are used. The reaction temperature is effectively from $-10°$ to $+50°$ C.

In a preferred embodiment sodium hydride is suspended in tetrahydrofuran and benzyl alcohol is added in doses. The 4-haloacetoacetic ester, dissolved in tetrahydrofuran, is added in doses into such solution. The most effective reaction temperature in that case is from $0°$ to $40°$ C.

After the reaction is completed, the tetrahydrofuran can be recaptured by distillation. The 4-benzyloxyacetoacetic ethyl ester produced according to this method of operation is a viscous oil with a $Kp_{0.5}$ of $135°$ to $136°$ C.

The hydrogenolysis can also be carried out in the presence of an acid. At the same time, the primary 4-hydroxyacetoacetic ester formed in situ is converted directly after its development into tetronic acid.

The preferred temperature for the hydrogenolysis is $0°$ to $30°$ C.

Hydrogenolysis is the cleavage of a bond in an organic compound with the simultaneous addition of a hydrogen atom to each fragment. (By hydrogenolysis one understands the decomposition of a compound with concurrent hydrogenation.) Hydrogenation is the combination of hydrogen with another substance, usually an unsaturated organic compound, and usually under the influence of temperature, pressure, and catalysts (usually nickel). The hydrogenolysis reaction is carried out effectively in the invention under pressure, e.g., 1 to 8 atm. Preferably, the hydrogenation treatment is carried out in the presence of a hydrogenation catalyst, such as, a noble metal. Examples of the noble metals are gold, silver, platinum, palladium, iridium, rhodium, ruthenium, osmium, cobalt, raney-nickel and others. In order to increase the reacting surface, such catalysts are applied effectively to carriers, for example, pumice stone, coal, silica gel, alumina and others, in order to increase the surface area.

The acid treatment of the 4-hydroxyacetoacetic ester forming as an intermediate product during or after the hydrogenolysis is accomplished effectively at a temperature of $0°$ to $30°$ C. Examples of acids which can be used are hydrochloric acid, trifluoroacetic acid, an acid cation exchanger, etc. Preferably hydrochloric acid in a semiconcentrated form is used.

Tetronic acid is 2,4-dioxo-tetrahydrofuran or $\beta$-ketobutyrolactone. Tetronic acid is useful as an accelerator for photographic development.

By way of summary, tetronic acid is produced starting out frotm 4-haloacetoacetic esters by way of the 4-benzyloxyacetoacetic ester.

EXAMPLE 1

7.56 g of 80 percent sodium hydride was freed of white oil by washing three times, each time with 30 ml of petroleum ether (boiling point: 40° to 60° C.). The sodium hydride was added to 160 ml of tetrahydrofuran. Then 14.28 g of benzyl alcohol was added in doses while stirring in such a way that a reaction temperature of 40° C. was maintained. After development of hydrogen was completed, a solution of 19.74 g (95.5 percent=0.1145 mole) of 4-chloroacetoacetic ethyl ester in 80 ml of tetrahydrofuran was added drop by drop over a 1 hour period. A temperature of 40° C. was maintained during such period. After 15 hours of stirring, whereby the temperature dropped to ambient temperature, half of the tetrahydrofuran was evaporated using the vacuum rotation evaporator. The still flowable residue was poured in a thin jet into a mixture of 14.3 g of concentrated HCl in 150 g of ice water, whereby the pH after conclusion of the addition adjusted itself to 5. Then such mixture was extracted 4 times with ether. After washing and drying, the ether was evaporated off during the vacuum rotation evaporator. The residue was distilled. 22.52 g (83.2 percent) of 4-benzyloxyacetoacetic ethyl ester (boiling point $Kp_{0.4}$ 126° C.) resulted.

21.24 g of the 4-benzyloxyacetoacetic ethyl ester dissolved in acetic ester (100 ml) was inserted into a 200 ml steel autoclave provided with a magnetic stirrer and was hydrogenolized in the presence of 1.05 g Pd 5 percent on coal with hydrogen with a pressure of 5 atm. After the reaction was completed, which amounted to a period of about 2 hours, and after a 2 hour post-reaction time, the catalyst was filtered out. The filtrate was evaporated on a vacuum rotation evaporator at 35° C. The residue was dried in the high vacuum. 13.4 g of 4-hydroxyacetoacetic ethyl ester in the form of a slightly yellowish oil resulted.

4.43 g of the 4-hydroxyacetoacetic ethyl ester was dissolved in 10 ml of 18 percent HCl and was stirred for 6 hours at ambient temperature. Subsequently the HCl was drawn off in the vacuum rotation evaporator at a temperature below 30° C. The crystalline residue was dissolved in a little water and the water was again drawn off in the vacuum rotation evaporator at a temperature below 30° C. This operation was once more repeated. There resulted 3.0 g of tetronic acid having a purity of 95.8 percent, which corresponded to a yield of 95.8 percent related to the 4-benzyloxy ester. The total yield, related to the 4-chloro ester, amounted to 79.7 percent.

EXAMPLE 2

4-benzyloxyacetoacetic ethyl ester was produced using the procedure of Example 1. The hydrogenolysis with Pd on coal, however, was carried out in the presence of ethanol as a solvent and in the presence of concentrated HCl. Tetronic acid resulted directly in a yield which was only a little below that of Example 1.

EXAMPLE 3

Sodium benzylate in tetrahydrofuran was reacted using the procedure of Example 1 with 4-chloroacetoacetic isopropyl ester. The resultant 4-benzyloxyacetoacetic acid isopropyl ester was subsequently hydrogenolyzed. The 4-hydroxyacetoacetic isopropyl ester thus formed was converted at ambient temperature into tetronic acid by treatment with 18 percent HCl. The total yield, related to the 4-chloroacetoacetic isopropyl ester, was 78 percent.

EXAMPLE 4

Using the procedure of Example 1, sodium benzylate was reacted in tetrahydrofuran with 4-chloroacetoacetic acid n-butyl ester. The resultant 4-benzyloxyacetoacetic acid-n-butyl ester was converted at ambient temperature into tetronic acid by treatment with 18 percent HCl. The total yield, related to the 4-chloroacetoacetic acid-n-butyl ester, was 76.5 percent.

What is claimed is:

1. Process for the production of tetronic acid from 4-haloacetoacetic ester comprising converting a 4-haloacetoacetic ester into the corresponding 4-benzyloxyacetoacetic ester, forming the 4-benzyloxyacetoacetic ester by hydrogenolysis into the corresponding 4-hydroxyacetoacetic ester, and converting the 4-hydroxyacetoacetic ester by treatment with acid into tetronic acid.

2. Process as claimed in claim 1 wherein the alkyl moiety in 4-haloacetoacetic acid alkyl ester has 1 to 4 carbon atoms.

3. Process as claimed in claim 2 wherein the 4-haloacetoacetic alkyl ester is 4-haloacetoacetic acid methyl ester.

4. Process as claimed in claim 2 wherein the 4-haloacetoacetic acid alkyl ester is 4-haloacetoacetic acid ethyl ester.

5. Process as claimed in claim 2 wherein the 4-haloacetoacetic acid alkyl ester is 4-chloroacetoacetic acid alkyl ester.

6. Process as claimed in claim 1 wherein the 4-benzyloxyacetoacetic ester is produced by conversion of 4-haloacetoacetic ester with a metal salt of benzyl alcohol.

7. Process as claimed in claim 6 wherein the conversion is conducted in the presence of an organic solvent.

8. Process as claimed in claim 7 wherein the metal salt is an alkali metal salt.

9. Process as claimed in claim 7 wherein the organic solvent is dimethyl sulfoxide or tetrahydrofuran.

10. Process as claimed in claim 6 wherein the conversion is conducted at a temperature of −10° to 50° C.

11. Process as claimed in claim 1 wherein the hydrogenolysis is carried out under pressure in the presence of a hydrogenation catalyst.

12. Process as claimed in claim 11 wherein the hydrogenolysis is conducted at a temperature of 0° to 30° C.

13. Process as claimed in claim 11 wherein the pressure is 1 to 8 atmospheres.

14. Process as claimed in claim 11 wherein the hydrogenation catalyst is a noble metal.

15. Process as claimed in claim 14 wherein the noble metal is palladium.

16. Process as claimed in claim 14 wherein the noble metal is on a carrier.

17. Process as claimed in claim 16 wherein the carrier is coal.

18. Process as claimed in claim 1 wherein the hydrogenolysis is carried out in the presence of an acid, whereby the 4-hydroxyacetoacetic ester forming in situ is rearranged directly into tetronic acid.

19. Process as claimed in claim 18 wherein the acid is a mineral acid.

20. Process as claimed in claim 18 wherein the acid is hydrochloric acid, trifluoroacetic acid or an acid cation exchanger.

21. Process as claimed in claim 1 wherein the 4-hydroxyacetoacetic ester is isolated before it is converted to tetronic acid.

22. Process as claimed in claim 8 wherein the alkali metal salt of benzyl alcohol is the sodium salt of benzyl alcohol.

* * * * *